(12) United States Patent
Funakoshi et al.

(10) Patent No.: US 9,710,738 B2
(45) Date of Patent: Jul. 18, 2017

(54) CELL COUNTING DEVICE INCLUDING A BODY WITH A DISPLAY AND AN EXTENSION TO RECEIVE A SAMPLE

(71) Applicant: OLYMPUS CORPORATION, Hachioji-shi, Tokyo (JP)

(72) Inventors: Yasuo Funakoshi, Hachioji (JP); Takumi Umemura, Hachioji (JP); Hideki Obuchi, Hachioji (JP); Yuki Yokomachi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/136,718

(22) Filed: Apr. 22, 2016

(65) Prior Publication Data

US 2016/0377523 A1 Dec. 29, 2016

(30) Foreign Application Priority Data

Jun. 23, 2015 (JP) ................................. 2015-126053

(51) Int. Cl.
| | |
|---|---|
| *G06K 15/00* | (2006.01) |
| *G06F 3/12* | (2006.01) |
| *G06F 3/041* | (2006.01) |
| *G01N 15/10* | (2006.01) |
| *G01N 15/14* | (2006.01) |

(52) U.S. Cl.
CPC ....... *G06K 15/404* (2013.01); *G01N 15/1468* (2013.01); *G06F 3/0412* (2013.01); *G06F 3/1243* (2013.01); *G01N 2015/1006* (2013.01); *G01N 2015/1486* (2013.01)

(58) Field of Classification Search
None
See application file for complete search history.

(56) References Cited

U.S. PATENT DOCUMENTS

| | | | | |
|---|---|---|---|---|
| 9,280,641 B2* | 3/2016 | Collins | ................. | G06F 3/1204 |
| 2004/0136581 A1* | 7/2004 | Ellis | ................... | G01N 15/1475 |
| | | | | 382/128 |
| 2005/0068019 A1* | 3/2005 | Nakamura | ................ | G06F 1/26 |
| | | | | 323/355 |
| 2006/0134793 A1* | 6/2006 | Key | .................... | G01N 33/5306 |
| | | | | 436/63 |
| 2006/0187442 A1* | 8/2006 | Chang | .................. | G01N 15/147 |
| | | | | 356/39 |
| 2008/0007781 A1* | 1/2008 | Oike | .................. | H04N 1/00278 |
| | | | | 358/1.16 |
| 2010/0104169 A1* | 4/2010 | Yamada | ............. | G01N 15/1429 |
| | | | | 382/134 |
| 2010/0149577 A1* | 6/2010 | Kamasuka | ......... | H04N 1/00222 |
| | | | | 358/1.13 |

(Continued)

*Primary Examiner* — Ming Hon
(74) *Attorney, Agent, or Firm* — Holtz, Holtz & Volek PC

(57) ABSTRACT

A cell counting device for counting the number of cells in a sample includes: an accommodation portion that accommodates, in a removable manner, at least a part of a holding member for holding the sample; and a display unit configured to display information including a result of counting of the number of cells. The display unit has a screen inclined with respect to a bottom of the cell counting device. The bottom is configured to be in contact with a placement surface on which the cell counting device is placed. The display unit is provided between the accommodation portion and the bottom.

17 Claims, 4 Drawing Sheets

(56) References Cited

U.S. PATENT DOCUMENTS

| | | | | |
|---|---|---|---|---|
| 2012/0314092 A1 | 12/2012 | Chu et al. | | |
| 2013/0182299 A1* | 7/2013 | Nakamura | ............... | B65H 3/06 |
| | | | | 358/498 |
| 2013/0335897 A1* | 12/2013 | Mochizuki | ............ | G06F 1/1601 |
| | | | | 361/679.01 |
| 2015/0092208 A1* | 4/2015 | Adachi | ................. | G06F 3/1276 |
| | | | | 358/1.13 |

* cited by examiner

CELL COUNTING DEVICE INCLUDING A BODY WITH A DISPLAY AND AN EXTENSION TO RECEIVE A SAMPLE

CROSS REFERENCES TO RELATED APPLICATIONS

This application is based upon and claims the benefit of priority from Japanese Patent Application No. 2015-126053, filed on Jun. 23, 2015, the entire contents of which are incorporated herein by reference.

BACKGROUND

1. Technical Field

The disclosure relates to a cell counting device for counting the number of cells in a sample.

2. Related Art

A cell counting device for counting the number of cells in a sample has been in widespread use in the related art (refer to US 2012/0314092 A, for example). A cell counting device disclosed in US 2012/0314092 A is configured to count the number of cells in a sample by accommodating a sample holder plate within the cell counting device through a slot holding the plate. Specifically, the cell counting device counts the number of cells by imaging the sample on the plate accommodated in the slot with use of an imaging optical system and performing image processing on the image. A count result is displayed on a display unit provided on a top surface of the cell counting device or printed and output by a printer included in the cell counting device.

SUMMARY

In some embodiments, a cell counting device for counting the number of cells in a sample includes: an accommodation portion that accommodates, in a removable manner, at least a part of a holding member for holding the sample; and a display unit configured to display information including a result of counting of the number of cells. The display unit has a screen inclined with respect to a bottom of the cell counting device. The bottom is configured to be in contact with a placement surface on which the cell counting device is placed. The display unit is provided between the accommodation portion and the bottom.

The above and other features, advantages and technical and industrial significance of this invention will be better understood by reading the following detailed description of presently preferred embodiments of the invention, when considered in connection with the accompanying drawings.

DETAILED DESCRIPTION

Embodiments of the present invention will now be described in detail with reference to the drawings. The present invention is not to be limited by the following embodiments. Each diagram referenced in the following description merely illustrates the shape, size, and positional relationship schematically for one to be able to understand the content of the present invention. That is, the present invention is not to be limited to the shape, size and positional relationship illustrated in each drawing.

Figure 1:
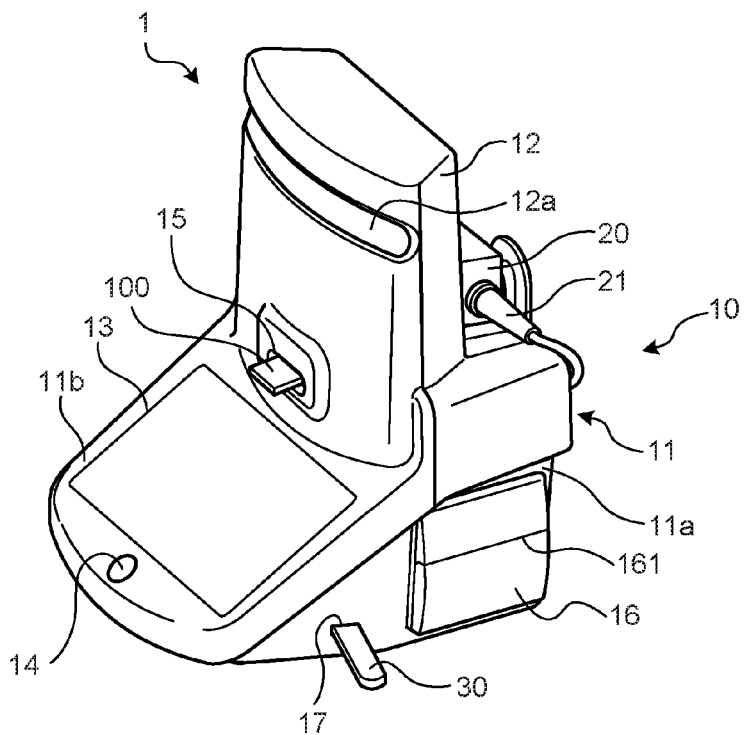
FIG. 1 is a perspective view illustrating a schematic configuration of a cell counting device according to an embodiment of the present invention.
Figure 2:
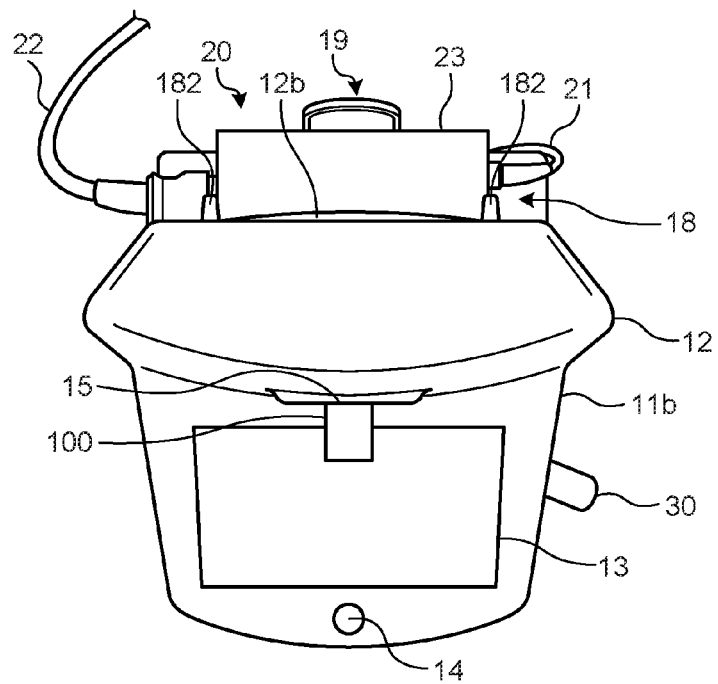
FIG. 2 is a top view illustrating a schematic configuration of the cell counting device according to the embodiment of the present invention.
Figure 3:
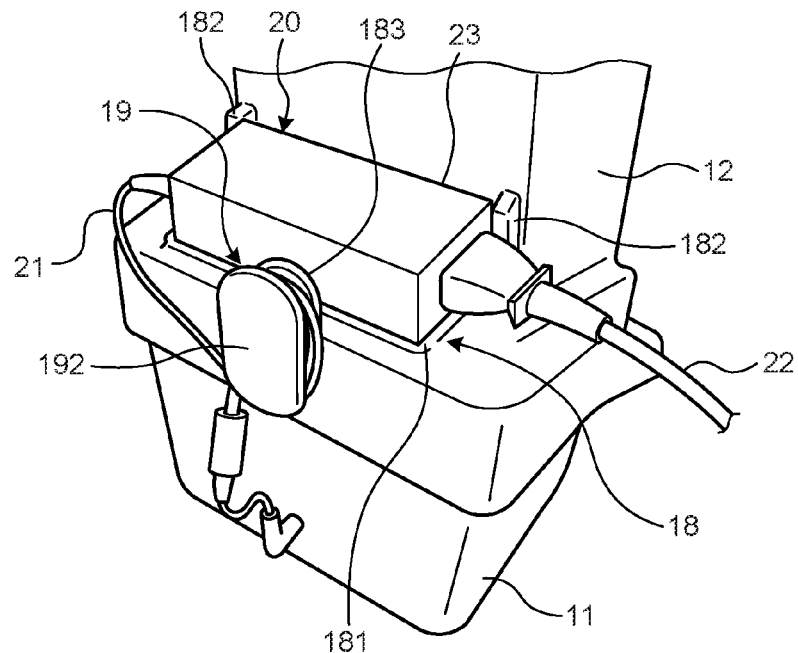
FIG. 3 is a perspective view illustrating a configuration of a principal part of the cell counting device according to the embodiment of the present invention.

FIG. 1 is a perspective view illustrating a schematic configuration of a cell counting device according to an embodiment of the present invention. FIG. 2 is a top view illustrating a schematic configuration of the cell counting device according to the embodiment. FIG. 3 is a perspective view illustrating a configuration of a principal part of the cell counting device according to the embodiment as seen from above a back surface of the cell counting device.

A cell counting device 1 illustrated in FIGS. 1 to 3 includes a cell counting unit 10 that counts the number of cells in a sample, a power cord 20 that supplies power to the cell counting unit 10, and a universal serial bus (USB) memory 30 that is a computer readable recording medium electrically connected to the cell counting unit 10.

A plate 100 (holding member) that holds a sample containing a cell to be counted is inserted into the cell counting unit 10 so that the sample is imaged by an imaging optical system inside the cell counting unit to count the number of cells in the sample and display as an image or print out a count result. A configuration of the cell counting unit 10 will be described later. Note that in the embodiment, a side of the cell counting unit 10 on which the plate 100 is inserted is referred to as the front and a side opposite to the front as the back in some cases.

As illustrated in FIGS. 2 and 3, the power cord 20 includes a direct current (DC) cable 21 connected to the cell counting unit 10, an alternating current (AC) cable 22 connected to an external outlet, and an AC adapter 23, one end of which is connected to the DC cable 21 and another end of which is connected to the AC cable 22. The AC adapter 23 has a prism-shaped casing to receive input of AC power through the AC cable 22 and output DC power corresponding to the cell counting unit 10 to the DC cable 21.

Figure 4:
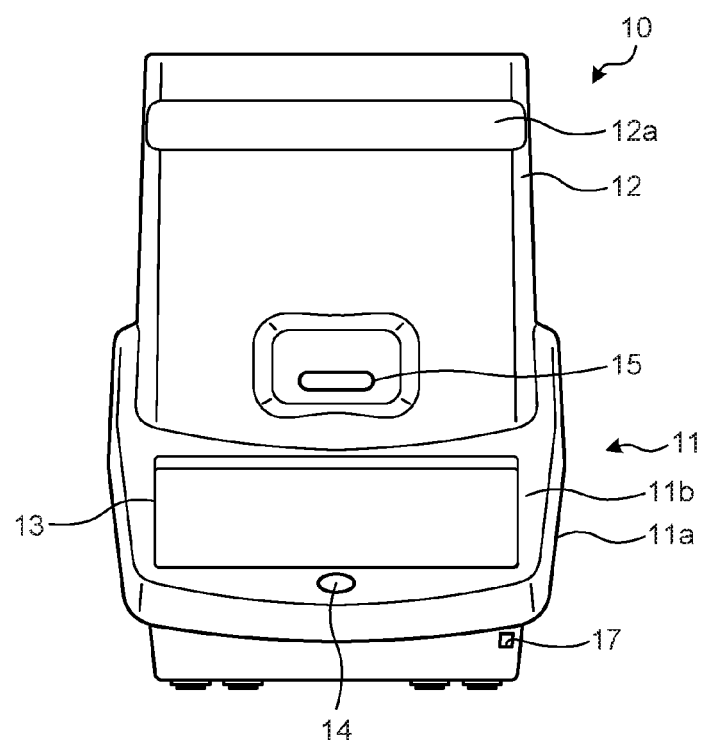
FIG. 4 is a front view illustrating a schematic configuration of a cell counting unit according to the embodiment of the present invention.
Figure 5:
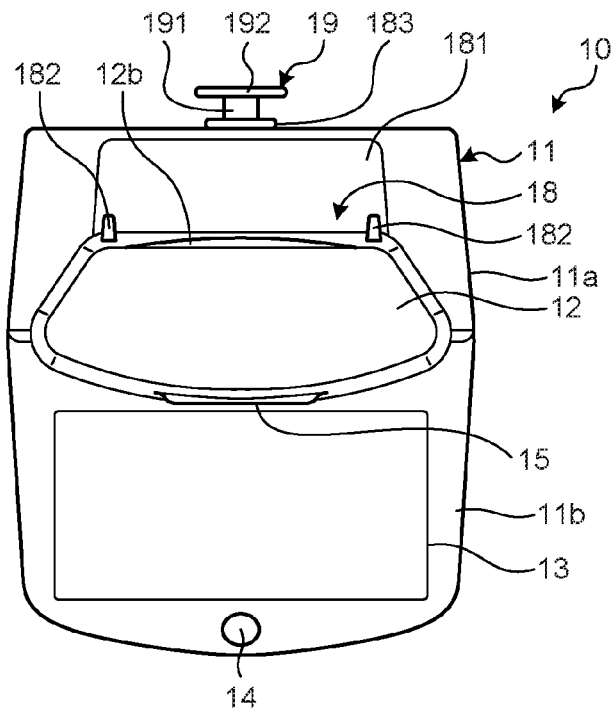
FIG. 5 is a top view illustrating a schematic configuration of the cell counting unit according to the embodiment of the present invention.
Figure 6:
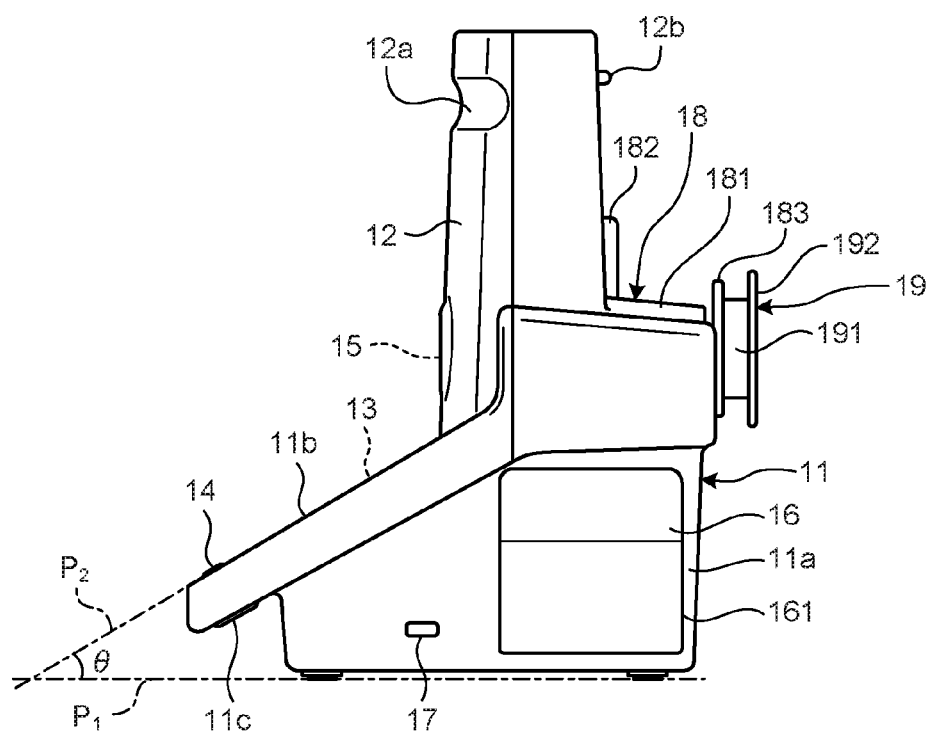
FIG. 6 is a side view illustrating a schematic configuration of the cell counting unit according to the embodiment of the present invention.
Figure 7:
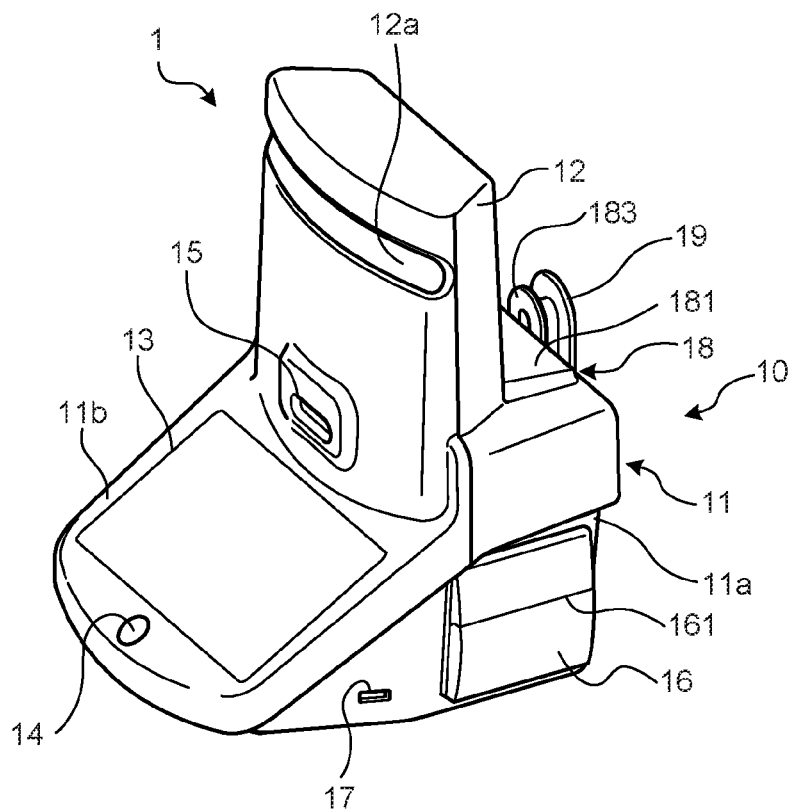
FIG. 7 is a perspective view illustrating a schematic configuration of the cell counting unit according to the embodiment of the present invention.
Figure 8:
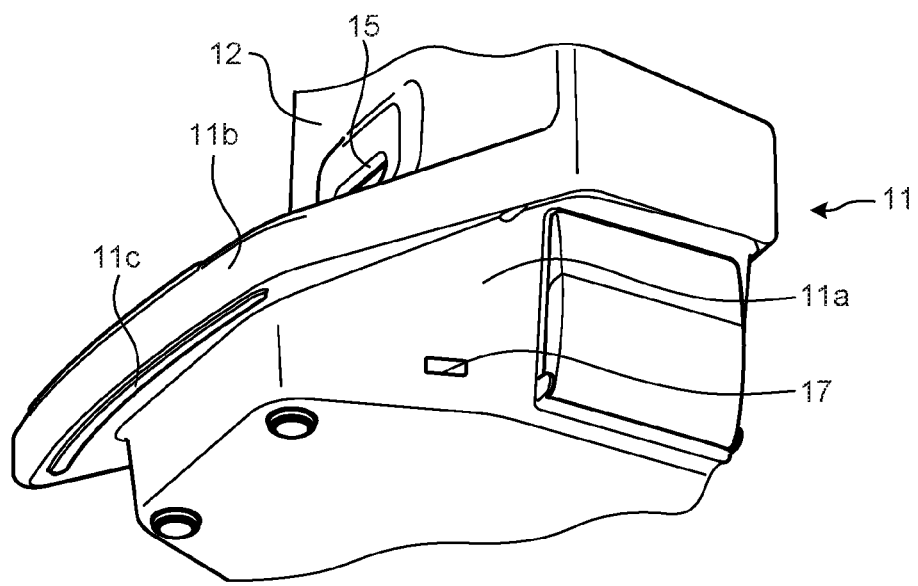
FIG. 8 is a lower perspective view illustrating a configuration of a principal part of the cell counting unit according to the embodiment of the present invention.

FIG. 4 is a front view illustrating a schematic configuration of the cell counting unit according to the embodiment. FIG. 5 is a top view illustrating a schematic configuration of the cell counting unit according to the embodiment. FIG. 6 is a side view illustrating a schematic configuration of the cell counting unit according to the embodiment. FIG. 7 is a perspective view illustrating a schematic configuration of the cell counting unit according to the embodiment. FIG. 8 is a lower perspective view illustrating a configuration of a principal part of the cell counting unit according to the embodiment.

The cell counting unit 10 includes a body portion 11 and an extension portion 12 making up a casing of the cell counting unit 10. The extension portion 12 extends upward from the body portion 11.

The body portion 11 includes a base 11a forming a foundation and an inclined portion 11b having an inclined plane inclined and extends downward from an upper part the base 11a. The base 11a of the cell counting unit 10 is placed on a placement surface such as a table when in use.

When the body portion 11 is placed on the placement surface such as the table, the inclined portion 11b is preferably disposed such that a plane $P_1$ passing through the bottom of the body portion 11 in contact with the placement surface and an inclined plane $P_2$ corresponding to the inclined plane of the inclined portion 11b and passing through a surface of a display screen of a display unit 13 (to be described) form an angle θ of 20° or larger and 40° or smaller. More preferably, the angle θ equals 25° or larger and 35° or smaller. When the inclined plane of the inclined portion 11b is disposed at the angle that falls within the aforementioned range, a user can easily check an image displayed on the display unit 13 when the user uses the cell counting unit 10 either while standing or sitting by a table on which the cell counting unit 10 is placed.

The inclined portion 11b has the display screen along the inclined plane and includes the display unit 13 displaying various information including a count result on the display screen and a power button 14 for receiving input for causing the cell counting unit 10 to be turned on or turned off. In the cell counting unit 10, the display unit 13 is arranged at a lower part (on a bottom side) of the cell counting unit 10 and between a slot 15 (to be described later) and the plane $P_1$. While the power button 14 is provided below the display unit 13 in the embodiment, the power button may be provided around the display unit 13.

The extension portion 12 extends vertically upward from the base 11a. The extension portion 12 is provided with the slot 15 (accommodation portion) which accommodates and holds a part of the plate 100 in a removable manner. In other words, the slot 15 is provided above the display unit 13. The slot 15 holds the plate 100 such that a surface of the plate 100 on which a sample is held is substantially orthogonal to the direction of gravity, namely parallel to the placement surface on which the cell counting unit 10 is placed. Note that an optical axis of the internal imaging optical system is substantially orthogonal to the placement surface of the sample and arranged at a position to pass through the sample while the plate 100 is inserted into the slot 15. While holding a part of the plate 100, the slot 15 accommodates a part including a sample holding area of the plate 100 inside the cell counting unit 10 and arranges the part in the imaging optical system (a counting area).

The cell counting unit 10 includes a light source for emitting illumination light that illuminates the sample, the imaging optical system including a lens and an image sensor, an image processing unit for performing predetermined image processing on image data generated by the imaging optical system, a recording unit recording or temporarily recording a program executed by the cell counting unit 10 and the image data generated by imaging performed by the imaging optical system as well as recording various information relevant to the cell counting unit 10, and a control unit including a central processing unit (CPU) or the like to exercise control over each unit included in the cell counting unit 10 (those units are not illustrated). The imaging optical system is arranged such that the optical axis thereof passes through the sample holding area of the plate 100 inserted into the slot 15.

The base 11a is further provided with a printer 16 for printing and outputting information including a count result, and a USB port 17 for holding one end of the USB memory 30 in a longitudinal direction in a removable manner. The printer 16 and the USB port 17 are provided on a side surface of the base 11a that is substantially orthogonal to a direction in which the inclined portion 11b is inclined to extend.

The printer 16 ejects printed paper (medium) to the side of the cell counting unit 10, namely in a direction orthogonal to the direction in which the inclined portion 11b extends. The printer 16 includes a cutter 161 configured to cut off printed matter being ejected. A blade of the cutter 161 extends in a front-back direction of the cell counting unit 10. As a result, a user holding printed matter can easily cut off the printed matter by pulling it toward the user.

While holding the USB memory 30, the USB port 17 supports the USB memory 30 such that a side (another end in the longitudinal direction) of the USE memory 30 opposite to the side inserted into the USB port 17 extends toward the front. In other words, the USE port 17 forms hollow space to accommodate the one end of the USB memory 30 in the longitudinal direction where, when a side of the extension portion 12 corresponding to the slot 15 corresponds to the front and a side opposite to the front corresponds to the back, the hollow space extends toward the back.

Moreover, an adapter holder 18 holding the AC adapter 23 and a winding portion 19 capable of winding therearound the DC cable 21 are provided at the back of the base 11a, namely on a side of the base 11a opposite to a side (corresponding to the display unit 13) where the inclined portion 11b extends.

The adapter holder 18 is provided on a top surface of the body portion 11 and includes a placement portion 181 forming a placement surface on which the AC adapter 23 is placed, two first projections (first projections 182) projecting from a side of the extension portion 12 opposite to a side on which the slot 15 is formed, and a second projection 183 projecting from the placement portion 181 in a direction orthogonal to the placement surface of the placement portion 181.

The first projections 182 are provided on opposing side surfaces or the like of the AC adapter 23, the side surfaces being connected to the DC cable 21 and the AC cable 22 of the AC adapter 23, respectively. The space between the first projections 182 is set according to a distance between side surfaces to be supported of the AC adapter 23 or, in the embodiment, between the side surfaces connected to the DC cable 21 and the AC cable 22 of the AC adapter 23.

The winding portion 19 extends from the base 11a to the back of the base 11a, and includes a shaft portion 191 forming a shaft around which the DC cable 21 is wound and a flat plate 192 provided at a distal end of the shaft portion 191 in its extending direction and having an area larger than that of a cross section of the shaft portion 191, the cross section being a plane orthogonal to the extending direction of the shaft portion. Note that the flat plate 192 is provided while facing the second projection 183. Therefore, the second projection 183, the shaft portion 191 and the flat plate 192 together form the shape of a bobbin.

The adapter holder 18 is configured such that the AC adapter 23 is placed in the placement portion 181 to be accommodated and held in hollow space formed by the placement portion 181, the first projections 182 and the second projection 183. The first projections 182 of the adapter holder 18 are in contact with the AC adapter 23 to prevent the AC adapter 23 from being disengaged from the side of the adapter holder 18. Moreover, a wall surface of the extension portion 12 and the second projection 183 are in contact with the AC adapter 23 to prevent the AC adapter 23 from being disengaged in the front-back direction of the adapter holder 18.

The DC cable 21 extending from the AC adapter 23 is wound around the shaft portion 191 of the winding portion 19, which stores an excess portion of the DC cable 21 while the AC adapter 23 is held in the adapter holder 18. Note that the winding portion 19 may also be adapted to store an excess portion of the AC cable 22 by winding the AC cable 22 around the shaft portion 191.

Moreover, the body portion 11 includes a first protrusion 11c (refer to FIG. 8) provided at the bottom an extended end of the inclined portion 11b and protruding from the bottom surface of the inclined portion 11b, while the extension portion 12 includes a recess 12a provided on the surface of the extension portion corresponding to the slot 15 and forming a recess on the surface and a second protrusion 12b provided on a back surface of the extension portion opposite to the surface on which the recess 12a is formed and protruding from the back surface.

When a user wishes to move the cell counting unit 10 while sliding it on a table, the user can easily pull the cell counting unit 10 toward the user by holding the first protrusion 11c from the front and pulling it. Moreover, when carrying the cell counting unit 10, a user can lift the unit while holding the recess 12a and the second protrusion 12b to be able to easily carry the cell counting unit 10. It is preferable in terms of ensuring the grip of a user that the second protrusion 12b on the back surface is provided at a position corresponding to the upper end of the recess 12a, and the surface of each of the first protrusion 11c, the recess 12a and the second protrusion 12b is processed to have a knurled pattern by knurling as well as coated to increase surface friction.

According to the embodiment described above, the cell counting unit 10 is adapted such that the display unit 13 is disposed below the slot 15, namely disposed on the bottom side of the cell counting unit 10, and at the same time the display screen on the display unit 13 is at an angle with respect to the placement surface on which the cell counting unit 10 is placed, whereby viewability can be ensured both when a user uses the unit while standing and when the user uses the unit while sitting.

Moreover, according to the embodiment described above, the cell counting unit 10 is adapted such that the display unit 13 is disposed on the bottom side of the cell counting unit 10, whereby the system can maintain stability even when the display unit 13 is increased in size or weight by enlarging the display screen to improve viewability or providing a touch panel on the display screen in the display unit 13. In order to maintain further stability against the aforementioned change in specifications of the display unit, it is preferable that the center of gravity of the display unit 13 corresponds with or is lower than the center of gravity of the cell counting unit 10.

Moreover, according to the embodiment described above, the power button 14 is disposed at the bottom of the cell counting unit 10 and in the vicinity of the display unit 13, whereby viewability of the power button 14 can be improved and, at the same time, the system's stability can be maintained when a load is applied to the cell counting unit 10 at the time the power button 14 is depressed. In contrast, when an operation button is disposed in an upper part as in the related art, depression of the operation button causes moment to be applied in a direction in which the cell counting device is inclined so that the stability cannot be maintained completely.

Moreover, if the touch panel is provided on the display unit 13 in the embodiment described above, members involved in an input operation such as the power button 14 and the touch panel are concentrated. It is therefore possible to provide the cell counting unit 10 with excellent operability.

Moreover, according to the embodiment described above, the adapter holder 18 of the cell counting unit 10 holds the AC adapter 23 while the winding portion 19 winds the DC cable 21 extending from the AC adapter 23 around the shaft portion 191 to store the excess portion of the DC cable 21, whereby the space occupied by the AC adapter 23 in the cell counting device 1 is cut to be able to save space for the cell counting device 1.

Moreover, according to the embodiment described above, the USB port 17 is adapted to support the USB memory 30 such that a side thereof opposite to the side inserted into the USB port 17 extends toward the front while the USB memory 30 is held in the port whereby, when a user uses the system with the display unit 13 and the slot 15 facing the user, the USB memory 30 extends from the base 11a toward the user so that the user can easily insert or remove the USB memory 30 into or from the USB port 17.

Moreover, according to the embodiment described above, the printer 16 is adapted to eject the printed paper to the side of the cell counting unit 10, namely in the direction orthogonal to the direction in which the inclined portion 11b extends, and include the blade extending in the front-back direction of the cell counting unit 10, whereby a user can easily cut off the ejected paper by just pulling the paper toward the user.

Note that while the plate 100 is used in the aforementioned embodiment, a member adapted to hold the sample to be observed such as a microplate may also be used as long as the slot 15 can be held.

Moreover, while the inclined portion 11b extends from the base 11a and is inclined at a certain angle in the aforementioned embodiment, the angle of the inclined portion 11b can be changed as well. In such case, the angle of inclination of the inclined portion 11b preferably falls within the angle range described above.

Moreover, while the display unit 13 is provided integrally with the body portion 11 in the aforementioned embodiment, the display unit 13 may also be provided in a detachable manner. The operability of the cell counting unit 10 can be further improved by detachably providing the display unit 13 and providing the touch panel in the display unit 13 to receive an input operation.

Moreover, in the aforementioned embodiment, the USB port 17 provided in the cell counting unit 10 may be adapted to be connected to a USB connector serving as a connector of a reader that reads information recorded in a flash memory such as the USB memory 30 as well as a computer readable recording medium such as a CD-ROM, a flexible disk (FD), a CD-R, or a digital versatile disk (DVD) and outputs the information being read. It may also be adapted to transmit the information being read to an external server or the like through a communication network. The communication network in this case can be an existing public network, local area network (LAN) or wide area network (WAN) and can be either wired or wireless.

According to some embodiments, it is possible to ensure the viewability both when the user uses the unit while standing and when the user uses the unit while sitting.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cell counting device for counting a number of cells in a sample, the cell counting device comprising:
a body including a display configured to display information including a result of counting of the number of cells, the display including a screen that is inclined with respect to a bottom of the cell counting device, and the bottom being configured to be in contact with a placement surface on which the cell counting device is placed; and
an extension that extends from the body and includes an accommodation portion configured to accommodate, in a removable manner, at least a part of a holding member for holding the sample;
wherein the extension comprises, at a distal end thereof, a recess and a protrusion on opposite sides of the extension;
wherein the display is provided between the accommodation portion and the bottom of the cell counting device; and
wherein the recess and the protrusion are located superior to the accommodation portion and the display.

2. The cell counting device according to claim 1, further comprising:
a power cord having an AC adapter; and
an adapter holder disposed on the extension on a side opposite to where the accommodation portion is provided, the adapter holder being configured to hold the AC adapter.

3. The cell counting device according to claim 2, wherein:
the power cord includes first and second cords which extend from the AC adapter, one of which is configured to be connected to a power source and the other of which is configured to be connected to the body, and
the cell counting device further comprises a winding member having a shaft around which at least one of the first and second cords is configured to be wound.

4. The cell counting device according to claim 2, wherein the adapter holder comprises:
a placement surface configured to have the AC adapter placed thereon; and
two projections which project from the side of the extension opposite to where the accommodation portion is provided, the two projections being positioned to be at opposite sides of the AC adapter when the AC adapter is placed on the placement surface.

5. The cell counting device according to claim 4, wherein the recess and the protrusion are located superior to the placement surface and the two projections.

6. The cell counting device according to claim 4, wherein the adapter holder further comprises a third projection which projects in a same direction as a direction in which the extension extends from the body, the extending direction of the third projection being orthogonal to the placement surface.

7. The cell counting device according to claim 6, further comprising:
a shaft which projects from the third projection; and
a plate provided at a distal end of the shaft;
wherein the third projection, the shaft, and the plate form a bobbin, wherein at least one of the first and second cords is configured to be wound around the shaft of the bobbin.

8. The cell counting device according to claim 1, further comprising a power button provided adjacent to the display and configured to receive input for causing the cell counting device to be turned on or turned off.

9. The cell counting device according to claim 8, wherein the power button is provided between the screen of the display and the bottom of the cell counting device.

10. The cell counting device according to claim 1, further comprising a printer configured to print the information including the result of the counting on a medium, and to eject the printed medium in a direction orthogonal (i) to a first direction in which the holding member is insertable into and removable from the accommodation portion and (ii) to a second direction in which the extension extends, the printer including a cutter that extends in the first direction and is configured to cut off the printed medium.

11. The cell counting device according to claim 10, wherein the printer is provided in the base.

12. The cell counting device according to claim 1, further comprising a port that has a hollow space which is configured to accommodate an end of a computer readable recording medium in a longitudinal direction thereof in a removable manner and is configured to be electrically connected to the recording medium, the hollow space extending toward a back of the extension which is opposite to a side opposite of the extension where the accommodation portion is provided.

13. The cell counting device according to claim 1, wherein the body includes:
a base having the bottom; and
an inclined portion that has the display, extends along the screen, and has a second protrusion which is provided at a distal end of the inclined portion and protrudes from a bottom surface of the inclined portion.

14. The cell counting device according to claim 1, wherein an inclination angle of the screen with respect to the bottom of the cell counting device is in a range of 20° to 40°, inclusive.

15. The cell counting device according to claim 14, wherein the inclination angle of the screen with respect to the bottom of the cell counting device is in a range of 25° to 35°, inclusive.

16. The cell counting device according to claim 1, wherein the recess and the protrusion are provided to have at least one of a knurled surface and a coating to increase surface friction.

17. The cell counting device according to claim 1, wherein a center of gravity of the display corresponds to or is lower than a center of gravity of the cell counting device as a whole.

* * * * *